(12) United States Patent
Feldschuh et al.

(10) Patent No.: US 9,002,656 B2
(45) Date of Patent: Apr. 7, 2015

(54) AUTOMATED TOTAL BODY ALBUMIN ANALYZER

(75) Inventors: Joseph Feldschuh, Riverdale, NY (US); Jonathan Feldschuh, New York, NY (US)

(73) Assignee: Daxor Corporation, New York, NY (US)

( * ) Notice: Subject to any disclaimer, the term of this patent is extended or adjusted under 35 U.S.C. 154(b) by 0 days.

(21) Appl. No.: 13/275,041

(22) Filed: Oct. 17, 2011

(65) Prior Publication Data

US 2013/0096836 A1 Apr. 18, 2013

(51) Int. Cl.
| | |
|---|---|
| *G06F 19/10* | (2011.01) |
| *G01D 18/00* | (2006.01) |
| *A61B 6/00* | (2006.01) |
| *A61B 5/0275* | (2006.01) |
| *A61B 5/145* | (2006.01) |
| *A61B 5/155* | (2006.01) |

(52) U.S. Cl.
CPC ............ *A61B 5/02755* (2013.01); *G06F 19/10* (2013.01); *A61B 5/1427* (2013.01); *A61B 5/14546* (2013.01); *A61B 5/155* (2013.01)

(58) Field of Classification Search
CPC ................................ G06F 19/10; G06F 19/345
See application file for complete search history.

(56) References Cited

U.S. PATENT DOCUMENTS

| | | | |
|---|---|---|---|
| 3,727,048 A | 4/1973 | Haas | |
| 4,055,083 A | 10/1977 | Haas | |
| 4,120,295 A | 10/1978 | Hill | |
| 4,197,836 A | 4/1980 | Wagner et al. | |
| 4,313,928 A | 2/1982 | Kato et al. | |
| 4,666,577 A | 5/1987 | Yamamoto et al. | |
| 5,024,231 A * | 6/1991 | Feldschuh et al. | 600/431 |
| 6,280,381 B1 | 8/2001 | Malin et al. | |
| 7,833,798 B2 | 11/2010 | Kubota et al. | |
| 2003/0211036 A1 | 11/2003 | Degani et al. | |
| 2005/0143628 A1* | 6/2005 | Dai et al. | 600/300 |
| 2006/0288253 A1* | 12/2006 | Kawamura et al. | 714/25 |
| 2008/0138846 A1 | 6/2008 | Kubota et al. | |
| 2009/0029391 A1 | 1/2009 | Engelebienne et al. | |
| 2010/0004178 A1 | 1/2010 | Assaly et al. | |

FOREIGN PATENT DOCUMENTS

| | | | |
|---|---|---|---|
| WO | 0185914 | A2 | 11/2001 |
| WO | 2010106140 | A1 | 9/2010 |

OTHER PUBLICATIONS

Rasmussen et al. Pflugers Arch., 363, 239-244, 1976.*
Martin Ellmerer et al., Measurement of interstitial albumin in human skeletal muscle and adipose tissue by open-flow microperfusion, 2000, pp. E352-E356, Am. J. Physiol. Endocrinol. Metab. vol. 278, Graz, Austria.
Carl A. Goresky et al., Indicator Dilution Measurements of Extravascular Water in the Lungs, 1969, pp. 487-501, vol. 48, The Journal of Clinical Investigation, Quebec, Canada.
James B. Bassingthwaighte et al., GENTEX, a general multiscale model for in vivo tissue exchanges and intraorgan metabolism, Apr. 19, 2006, pp. 1423-1442, vol. 364, Philosophical Transactions of The Royal Society, Seattle, USA.
W. P. T. James et al., Albumin Metabolism: Effect of the Nutritional State and the Dietary Protein Intake, 1968, pp. 1958-1972, vol. 47, The Journal of Clinical Investigation, Kingston, Jamaica.
Warren L. Beeken, Studies of I131_Albumin Catabolism and Distribution in Normal Young Adult Males, Jan. 25, 1960, vol. 41, No. 6, Journal of Clinical Investigation, Seattle, USA.
Wikipedia, Local Regression, http://en.wikipedia.org/wiki/Local_regression, Feb. 17, 2011, Wikipedia, USA.
Excerpt, Daxor Corporation 10K (1986), pp. 1 and 5-6.
The Wall Street Journal, Jan. 16, 1986, p. 13, and New York Newsday, Jan. 15, 1987.
Daxor Corporation, Annual Report (1985), p. 6.
Daxor Corporation, Annual Report (1986), pp. 1-2.
The Newsletter of Innovation—Breakthrough—by Boardroom Reports, vol. IV, No. 22 (Nov. 15, 1986).
"Problems of Probability Theory, Mathematical Statistics and Theory of Random Functions," edited by A.A. Sveshnikov, pp. 325-329, 1968.
Feldschuh et al., Circulation, vol. 56, No. 4, Oct. 1977, pp. 605-612.
Mollisan, Brit J. of Haematology, vol. 25, 1973, pp. 801-814.
Tishchenko et al., Meditsinkskaya Tekhnika, No. 1, Jan. Feb. 1980, pp. 39-42.
International Search Report of PCT/US2012/060613 dated Feb. 12, 2013.
Written Opinion of PCT/US2012/060613 dated Feb. 12, 2013.

* cited by examiner

*Primary Examiner* — Michael Borin
(74) *Attorney, Agent, or Firm* — Amster, Rothstein & Ebenstein LLP

(57) ABSTRACT

A computer-based method for automatically determining total body albumin of a living being based on the calculated intravascular albumin, the calculated observed ratio of amount of albumin in the intravascular system to amount of albumin in the extravascular system at the first time, and the baseline of expected ratio of amount of albumin in the intravascular system to amount of albumin in the extravascular system at the first time.

3 Claims, 4 Drawing Sheets

AUTOMATED TOTAL BODY ALBUMIN ANALYZER

TECHNICAL FIELD

The present invention relates to systems and methods for analyzing total body albumin of a living being.

SUMMARY OF THE INVENTION

A computer-based method for automatically determining total body albumin of a living being according to an exemplary embodiment of the present invention comprises the steps of: determining a baseline of expected ratio of amount of albumin in an intravascular system of the living being to amount of albumin in an extravascular system of the living being; determining albumin concentration of the living being; calculating, using one or more processors, plasma volume of the living being based on detected counts of radio-labeled albumin injected into the living being; calculating, using one or more processors, an amount of intravascular albumin within the living being based on the calculated plasma volume and the determined albumin concentration; calculating, using one or more processors, an observed ratio of amount of albumin in the intravascular system of the living being to amount of albumin in the extravascular system of the living being at a first time after injecting the radio-labeled albumin into the living being; and calculating, using one or more processors, the total body albumin of the living being based on the calculated intravascular albumin, the calculated observed ratio of amount of albumin in the intravascular system of the living being to amount of albumin in the extravascular system of the living being at the first time, and the baseline of expected ratio of amount of albumin in the intravascular system of the living being to amount of albumin in the extravascular system of the living being at the first time.

In at least one embodiment, the method further comprises the steps of: calculating, using one or more processors, an observed ratio of amount of albumin in the intravascular system of the living being to amount of albumin in the extravascular system of the living being at a second time after injecting radio-labeled albumin into the living being, the second time being later than the first time; calculating, using one or more processors, the total body albumin of the living being based on the determined intravascular albumin, the observed ratio of amount of albumin in the intravascular system of the living being to amount of albumin in the extravascular system of the living being at the second time, and the baseline of expected ratio of amount of albumin in the intravascular system of the living being to amount of albumin in the extravascular system of the living being at the second time; and calculating, using one or more processors, an average value of the total body albumin calculated at the first and second times.

In at least one embodiment, the second time is approximately 24 hours after the first time.

In at least one embodiment, the step of determining a baseline of expected ratio of amount of albumin in an intravascular system of the living being to amount of albumin in an extravascular system of the living being comprises the steps of: collecting data related to count values of radio-labeled albumin over a period of time after the radio-labeled albumin is injected into a plurality of living beings; and generating a baseline curve based on a locally weighted scatterplot smoothing analysis of the data.

In at least one embodiment, the step of calculating plasma volume of the living being is performed using an automated blood volume analyzer.

An automated total body albumin analyzer according to an exemplary embodiment of the present invention comprises: means for receiving input of first data related to a baseline of expected ratio of amount of albumin in an intravascular system of the living being to amount of albumin in an extravascular system of the living being; means for receiving input of second data related to albumin concentration of the living being; means for calculating plasma volume of the living being based on detected counts of radio-labeled albumin injected into the living being; means for calculating an amount of intravascular albumin within the living being based on the calculated plasma volume and the albumin concentration of the living being; means for calculating an observed ratio of amount of albumin in the intravascular system of the living being to amount of albumin in the extravascular system of the living being at at least one time after injecting the radio-labeled albumin into the living being; and means for calculating the total body albumin of the living being based on the calculated intravascular albumin, the calculated observed ratio of amount of albumin in the intravascular system of the living being to amount of albumin in the extravascular system of the living being at the at least one time, and the baseline of expected ratio of amount of albumin in the intravascular system of the living being to amount of albumin in the extravascular system of the living being at the at least one time.

In at least one embodiment, the at least one time comprises multiple times, and the automated total body albumin analyzer further comprises a means for calculating an average value of the total body albumin calculated at the multiple times.

In at least one embodiment, the baseline is a baseline curve based on a locally weighted scatterplot smoothing analysis of data related to count values of radio-labeled albumin over a period of time after the radio-labeled albumin is injected into a plurality of living beings.

In at least one embodiment, the means for calculating plasma volume is an automated blood volume analyzer.

A system for automatically determining total body albumin of a living being according to an exemplary embodiment of the present invention comprises: one or more data processing apparatus; and a computer-readable medium coupled to the one or more data processing apparatus having instructions stored thereon which, when executed by the one or more data processing apparatus, cause the one or more data processing apparatus to perform a method comprising: receiving first data related to a determined baseline of expected ratio of amount of albumin in an intravascular system of the living being to amount of albumin in an extravascular system of the living being; receiving second data related to determined albumin concentration of the living being; calculating plasma volume of the living being by detecting counts of radio-labeled albumin injected into the living being; calculating an amount of intravascular albumin within the living being based on the determined plasma volume and the determined albumin concentration; calculating an observed ratio of amount of albumin in the intravascular system of the living being to amount of albumin in the extravascular system of the living being at a first time after injecting the radio-labeled albumin into the living being; and calculating the total body albumin of the living being based on the calculated intravascular albumin, the calculated observed ratio of amount of albumin in the intravascular system of the living being to amount of albumin in the extravascular system of the living being at the first time, and the baseline of expected ratio of amount of albumin in the intravascular system of the living being to amount of albumin in the extravascular system of the living being at the first time.

These and other features and advantages of the present invention will be presented in more detail in the following detailed description and the accompanying figures which illustrate by way of example principles of the invention.

BRIEF DESCRIPTION OF THE DRAWINGS

Various exemplary embodiments of this invention will be described in detail, with reference to the following figures, wherein.

DESCRIPTION OF PREFERRED EMBODIMENTS OF THE INVENTION

Albumin is a crucial protein in the bloodstream. The concentration of albumin can be readily determined by a relatively simple lab test on a patient's blood sample, but the TBA is also of clinical interest. Determining TBA from the measured albumin concentration requires knowledge of the plasma volume and the ratio of albumin in the extravascular system to the albumin in the intravascular system.

Various exemplary embodiments of the present invention are directed to a system and method for determining total body albumin (TBA) using a tracer dilution technique. According to at least one embodiment, a tracer is injected into the blood stream of a living being, and a plurality of mixed samples of blood and tracer are removed from the blood stream at a corresponding plurality of measured time intervals subsequent to the injecting step. A ratio of intravascular albumin to extravascular albumin corresponding to each time interval is automatically calculated from the tracer level in the mixed samples, and an adjusted time-zero TBA is automatically calculated from the calculated ratio values and time intervals, using a comparison to a baseline decay curve.

Figure 1:
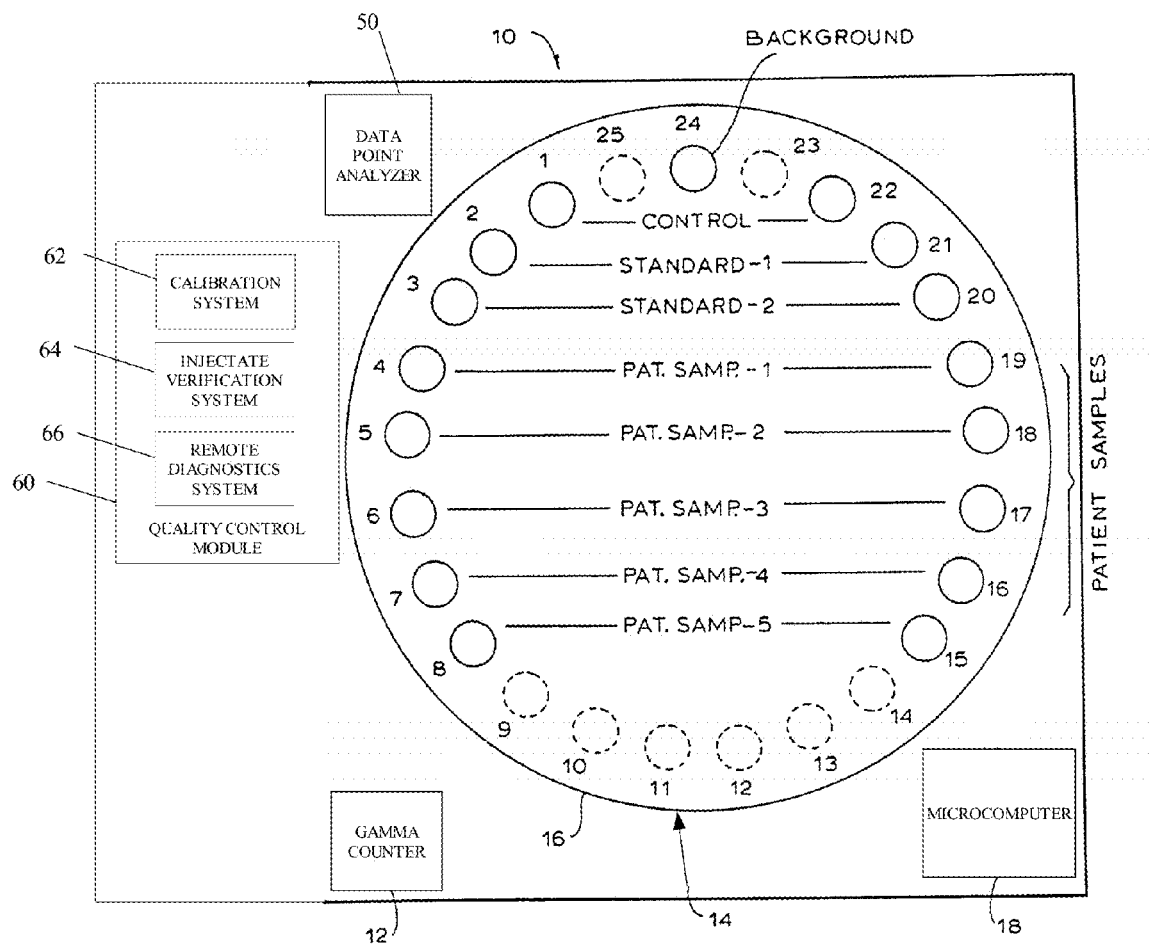
FIG. 1 is a total body albumin analyzer according to an exemplary embodiment of the present invention.

Various exemplary embodiments of the methods according to the present invention may be implemented using an automated blood volume analyzer, such as the automated multipoint blood volume analyzer described in U.S. Pat. No. 5,024,231, the contents of which are incorporated herein by reference in their entirety. In this regard, a block diagram of the blood volume analyzer disclosed in U.S. Pat. No. 5,024,231, modified so that the blood volume analyzer may also function as a total body albumin analyzer, is shown in FIG. 1. The automated total body albumin analyzer, generally designated by reference numeral 10, includes analyzer hardware such as, for example, an NaI scintillation gamma counter 12, an automatic sample feed mechanism 14 (including a sample holder 16 having spaces 25 for test tubes) and a microcomputer 18 running dedicated hardware and/or software. The microcomputer 18 includes a keyboard or other data entry unit and a liquid crystal display, printer or other data display unit. In general, the analyzer 10 is a computer-controlled instrument for the direct measurement of human blood volume and associated quantities, as well as for the measurement of TBA. The direct measurement of blood volume is based on the method of tracer dilution utilizing I-131-tagged serum albumin. The analyzer measures the extent to which the radioactive tracer is diluted when it is dispersed in the patient's bloodstream. The success of the measurement depends on the ability of the circulatory system to distribute the tracer evenly, so that a quantitative measure of dilution can be made. Each sample extracted from the patient after injection with the tracer represents the tracer as diluted into the plasma volume of the patient. The plasma volume is calculated based on the counts measured from a patient's samples, environment background samples, standard samples and control samples. The hematocrit is used to convert the plasma volume to whole blood volume.

According to various exemplary embodiments of the present invention, the automated total body albumin analyzer 10 may include additional functionality that enables for processing of appropriate data to calculate TBA according to the various exemplary embodiments of the inventive method. For example, the automated total body albumin analyzer 10 may include appropriate hardware components to carry out the various steps of the inventive method, and/or the automated total body albumin analyzer may include programming encoded on computer readable media that when read by a computer processor causes the computer processor to carry out the various steps of the method according to various exemplary embodiments of the present invention. In this regard, the total body albumin analyzer 10 may include at least one memory, at least one processor and at least one processor readable media.

The conventional method for measuring TBA is relatively time-consuming. The conventional procedure is based on the indicator-dilution technique in which radioactive albumin I-131 is injected into a patient. As disclosed in U.S. Pat. No. 5,024,231, the initial plasma volume is determined from the short-term (over the course of an hour) disappearance of the I-131 tracer based on the counts measured from a patient's samples, environment background samples, standard samples and control samples. The tracer disappears from the blood stream according to a complicated curve showing the presence of multiple loss rates. This is due to the multiple destinations for the labeled albumin. For example, the labeled albumin may be excreted in urine, absorbed by tissues or mixed with the extravascular fluid. To find the ratio of the extravascular to intravascular albumin, according to the conventional method, it is necessary to wait until the concentrations have stabilized in and out of the blood stream, and the decay follows a simple log-linear function. The log-linear portion of the curve does not start until two or three days after injection, and to get a reliable extrapolation to time zero, it is necessary to have multiple samples over subsequent days. However, it is of much more clinical interest to have a TBA measurement available in a shorter time frame.

Figure 2:
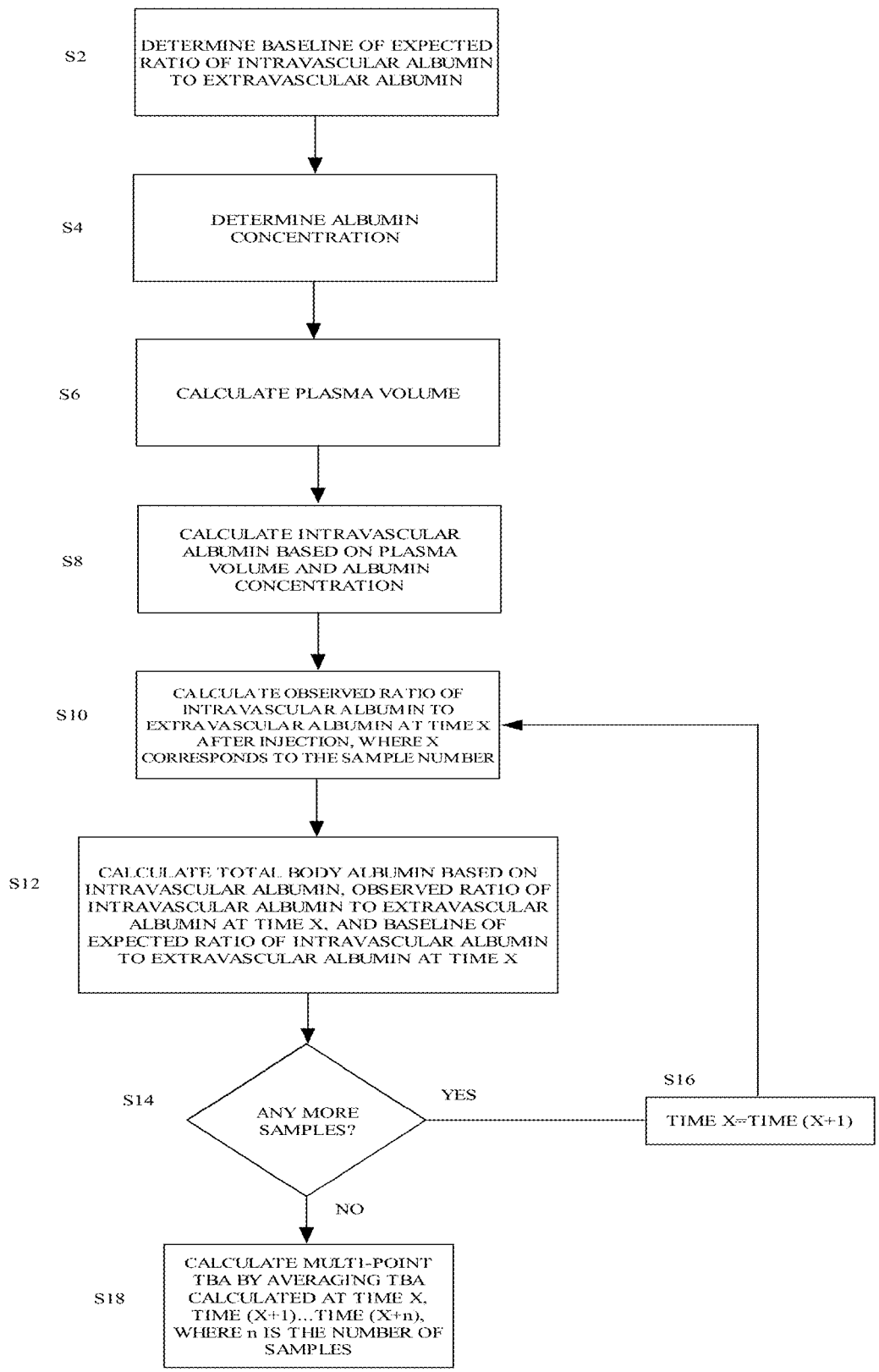
FIG. 2 is a flow chart showing a method of calculating total body albumin according to an exemplary embodiment of the present invention.
Figure 3:
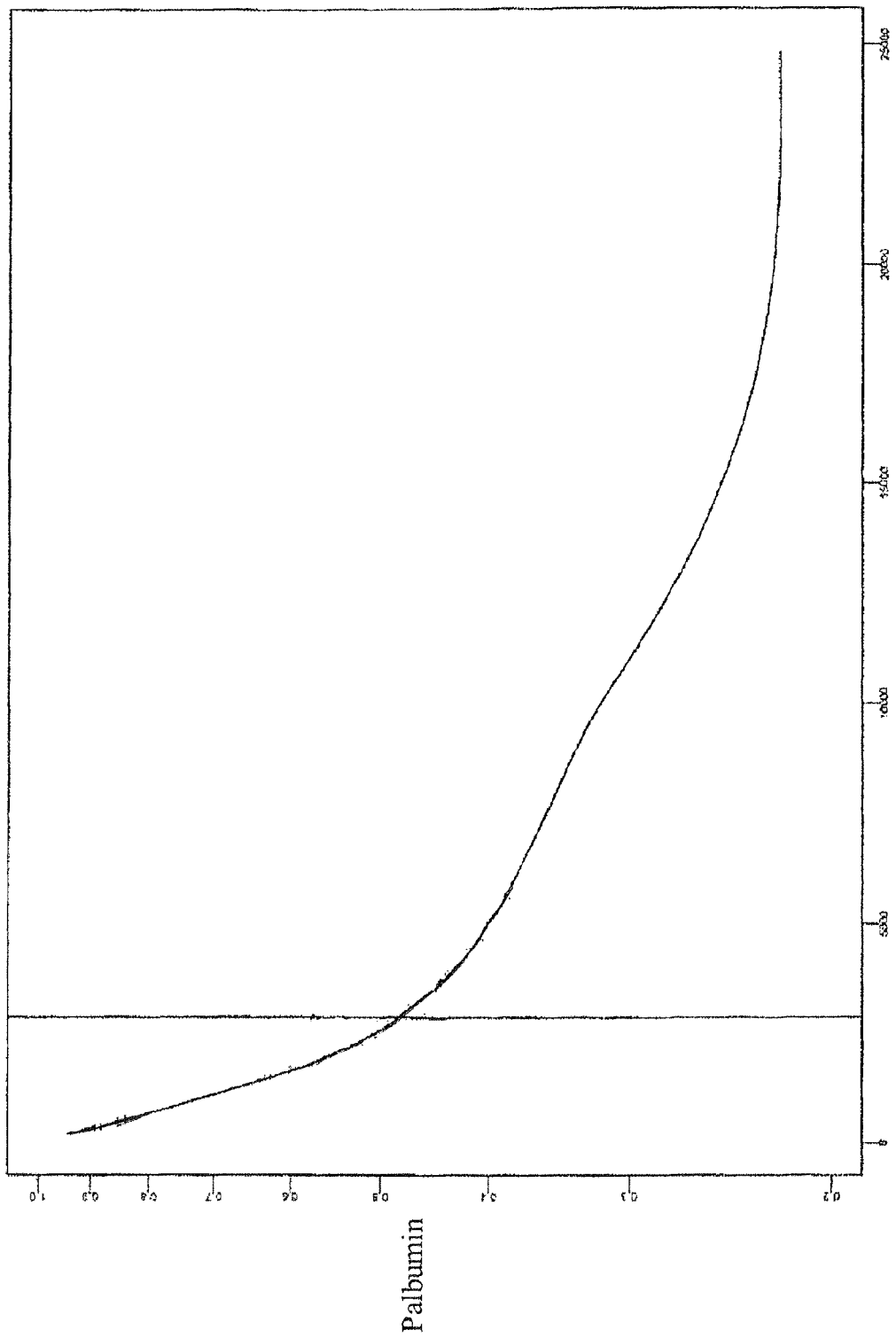
FIG. 3 is a baseline curve of ratio of intravascular to extravascular albumin according to an exemplary embodiment of the present invention.

FIG. 2 is a flow chart showing a method of calculating TBA according to an exemplary embodiment of the present invention. In step S2 of the method, a baseline of the expected ratio of the amount of intravascular albumin to the amount of extravascular albumin is determined using experimental data. The baseline may be determined using a locally smoothed exponential fit (LOESS) to the decay curve of radiolabeled albumin. The decay curve may be obtained by injecting a plurality of normal volunteers with radio-labeled albumin I-131, collecting blood samples over a time period after injection, and gathering data related to number of counts of albumin I-131 within each sample. The count data indicates the intravascular albumin counts over time. The data may be plotted on a "time-elapsed" vs. "Palbumin" graph, where Palbumin is the ratio of counts at a specified time to the initial counts at time zero. A LOESS analysis may be performed on the data to generate a curve that defines the baseline ratio of intravascular to extravascular albumin. An exemplary baseline curve is show in FIG. 3. It has been found from the data that patient samples exhibited a consistent deviation from the average curve. That is, the patient data tracked consistently above, below or along the baseline curve. This provides confidence that the patient's time-zero extrapolated values can be inferred from the complex, early part of the curve, rather than waiting for the later, log-linear portion of the curve by taking into account the deviation between the patient's data and the baseline curve.

In step S4, the patient's albumin concentration is determined using lab tests known to those of ordinary skill in the art. For example, a suitable lab test for determining albumin concentration may be a component of liver function tests (LFTs), but may be ordered separately. Albumin can be measured in serum (yellow-top tube), plain tube with no additives (red-top tube), or heparin plasma (green-top tube). One of the methods used is bromocresol green on a Roche Modular or Olympus AU2700 analyzer.

In step S6, the patient's plasma volume is determined using the automated multi-point blood volume analyzer functionality of the total body albumin analyzer 10 described above and shown in FIG. 1. In this regard, the automated total body albumin analyzer may derive the patient's plasma volume by comparing the count from the patient's sample (minus the count from the control sample) to the count from the standard sample (minus the count from the background).

In step S8, the intravascular albumin of the patient is calculated using the determined values for albumin concentration and plasma volume. In particular, the intravascular albumin may be calculated using the following formula:

$$\text{albumin.IV} = \text{albumin concentration} * \text{plasma volume} \quad (1)$$

In step S10, the observed ratio of intravascular albumin to extravascular albumin at time X after injection of radio-labeled albumin is calculated, where X corresponds to the patient sample number. In this step, the total body albumin analyzer may automatically collect the count data corresponding to the time X sample using the gamma counter 12, and then calculate the observed count data to the initial count data at time zero. Any number of patient samples may be collected, such as, for example, one patient sample, in which case a one-point albumin measure may be determined, or multiple samples, in which case a multi-point albumin measure may be determined. In this regard, the uncertainty of the TBA measurement improves as the length of time increases between injection and measurement, but not by a very large factor. For most patients, a single-point TBA measurement, taken between 24 and 48 hours after initial injection, would suffice.

In step S12, the patient's TBA is calculated based on the values for intravascular albumin, observed ratio of intravascular albumin to extravascular albumin at time X, and the baseline of expected ratio of intravascular albumin to extravascular albumin at time X. In this step, the total body albumin analyzer may automatically calculate TBA using the following formulas:

$$\text{Palbumin.deviation} = (\text{Palbumin.observed} - \text{Palbumin.expected})/\text{Palbumin.expected} \quad (2)$$

$$\text{albumin.IV/TBA.ratio.implied} = \text{albumin.IV/TBA.ratio.baseline} * (1 + \text{Palbumin.deviation}) \quad (3)$$

$$\text{TBA} = \text{albumin.IV}/(\text{albumin.IV/TBA.ratio.implied}) \quad (4)$$

where,

Palbumin.deviation is the standard deviation of the observed Palbumin from the expected Palbumin from the baseline curve at time X;

albumin.IV/TBA.ratio.implied is the implied ratio of intravascular albumin to TBA;

albumin.IV/TBA.ratio.baseline, which is assumed to be an average value (i.e., 32.79%)

In step S14, it is determined whether there are any more patient samples. If so, the process continues to step S16, where time X is set equal to time (X+1), where time (X+1) corresponds to the time at which the next sample is taken. The process then jumps back to step S10, where the observed ratio of intravascular albumin to extravascular albumin is determined based on the count data collected from the next sample. TBA is then calculated once again based on the observed ratio and the baseline curve data.

If it is determined that there are no more samples in step S14, the process continues to step S18, where a multi-point TBA measure may be calculated by averaging the previously calculated TBA measures corresponding to each of the samples. It should be appreciated that, according to exemplary embodiments of the present invention, the multi-point TBA measure may be calculated before TBA measures have been calculated for all samples.

In exemplary embodiments of the present invention, a preliminary TBA measure may be calculated as soon as plasma volume and albumin concentration data is available. This calculation simply measures the intravascular albumin using the known plasma and albumin concentration, and the patient is assumed to have an average ratio of intravascular albumin to total body albumin. The preliminary TBA may be calculated using the following formula:

$$\text{preliminary.albumin.total} = \text{albumin.IV}/(\text{albumin.IV/TBA.baseline}) \quad (5)$$

As further shown in FIG. 1, the blood volume/total body albumin analyzer 10 according to an exemplary embodiment of the present invention may include a data point analyzer 50 that ensures the accuracy of the patient sample readings. These samples are subject to "normal" variation due to the limits of precision of the various collection and measurement procedures involved. However, samples are occasionally corrupted by gross errors of collection and measurement. Objects according to an exemplary embodiment of the invention include both detection of such errors and prevention of the reporting of an inaccurate final result, correction of these errors by eliminating the suspect measurements, and reporting a valid final measurement. This correction mechanism is quite medically significant, as the test itself is time-consuming, expensive, involves exposure to radiation, and is often performed on patients in critical or dynamic conditions, where doctors need the test results to decide on a course of care.

According to an exemplary embodiment of the present invention, the data point analyzer 50 may perform an algorithm on the patient data points to determine the accuracy of the points. The algorithm may use a combination of statistical measures determined using an extensive database of actual patient results. The actual patient results may be obtained by conducting a study using a database of blood volume tests. An aim of the study is to establish normal values for the transudation slope and the uncertainty of the regression (and, by extension, of the final blood volume results) for cases that were considered to be free of "bad" points. A case is determined to be "good" or "bad" based on visual examination of the time zero regression graphs. For each case, two standard statistical measures of the "goodness" of the regression may be made, as follows:

1. Residual Standard Error (RSE), which provides a measure of the uncertainty of the regression (i.e., of the time-zero intercept and the transudation slope); and
2. R-Squared (RSQ), which provides a measure of the percentage of the variance of the individual points which is explained by the regression (i.e., how well does a straight line fit the data).

An RSE of 0% indicates a perfect straight-line regression, and an RSQ of 100% indicates a perfect straight-line regression.

An exemplary study includes 74 "good" and 17 "bad" cases, and results in the statistical data shown in Table 1:

TABLE 1

|  | SLOPE | RSQ | RSE |
|---|---|---|---|
| MEAN | 0.206% | 76% | 1.06% |
| MEDIAN | 0.198% | 87% | 1.06% |
| STANDARD DEVIATION | 0.115% | 24% | 0.68% |

The above results indicate for the exemplary study an average transudation slope of 0.206%±0.115% min$^{-1}$. The average RSE for the study is a little more than 1%, although the median is a little less (the distribution is somewhat skewed from normal because RSE can never be less than zero). The results for RSQ are similar to RSE, in that the median case is better than the average one.

The data point analyzer 50 may perform an algorithm that takes as input a range for Acceptable Slope and a range for Acceptable RSE. The acceptable ranges may be chosen based on the results of the previously described exemplary study. For example, an Acceptable Slope may be chosen to be between 0% and 0.6%, and an Acceptable RSE may be chosen to be less than 2.5%. For each patient, a set of data points may be collected, and the data point analyzer 50 may automatically calculate a regression for first the full set of data points, and then calculate a number of additional regressions for the set with each regression calculated with a different data point removed. The data point analyze 50 may calculate the slope, RSE and RSQ for each regression. The regression that exhibits a combination of the best RSQ, the best RSE, an Acceptable RSE and an Acceptable Slope may be selected by the data point analyzer 50 as the most accurate regression for the patient data set. If none of the regressions satisfy these criteria, then if any of the regressions involving a removed data point satisfies the best RSE, an Acceptable RSE and an Acceptable Slope criteria, then that regression is selected as the most accurate. Otherwise, the full data set regression is selected. If the full data set regression does not have an Acceptable Slope or an Acceptable RSE, the data point analyzer 50 may issue a warning.

The following example illustrates the bad points removal algorithm as performed by the data point analyzer 50 according to an exemplary embodiment of the present invention:

Example 1

Figure 4:
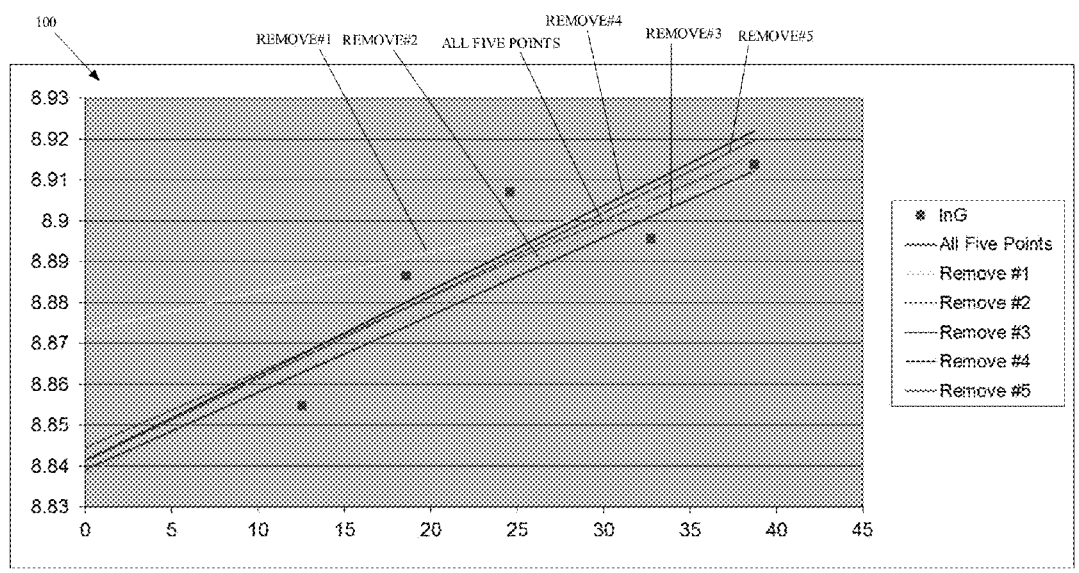
FIG. 4 is a chart illustrating various regressions calculated using the total body albumin analyzer according to an exemplary embodiment of the present invention.

An automated multi-point blood volume analyzer was used to measure blood volume of Patient A using five different samples of Patient A's blood collected at different time intervals after Patient A was injected with tracer. The five data points are plotted in chart 100 shown in FIG. 4, and summarized in Table 2. In particular, the values listed in the row labeled "InG" in Table 2 and the data points plotted in chart 100 indicate natural log values of Patient A's calculated total blood volume. A regression was calculated by the data point analyzer of the automated multi-point blood volume analyzer using first all five data points, and the results are listed under the column labeled "All Five Points" in Table 2 and illustrated by the line labeled "All Five Points" in chart 100. Subsequent regressions were then calculated by the data point analyzer, with each regression calculated with a different data point removed. In chart 100, the line labeled "Remove #1" corresponds to a regression performed with data point #1 removed, the line labeled "Remove #2" corresponds to a regression performed with data point #2 removed, the line labeled "Remove #3" corresponds to a regression performed with data point #3 removed, the line labeled "Remove #4" corresponds to a regression performed with data point #4 removed, and the line labeled "Remove #5" corresponds to a regression performed with data point #5 removed. The regression having the best RSQ is the one calculated with data point #3 removed. However, that regression does not exhibit the best RSE. Thus, none of the regressions exhibit a combination of the best RSQ and the best RSE. The data point analyzer 50 then selected the regression with point #1 removed, since that regression exhibited the best RSE while having acceptable values for slope and RSE.

TABLE 2

| Sample # | Time | UnadjVol | InG | All Five Points | Remove #1 | Remove #2 | Remove #3 | Remove #4 | Remove #5 |
|---|---|---|---|---|---|---|---|---|---|
| 0 | 0 |  |  | 8.8444 | 8.8731 | 8.8379 | 8.8391 | 8.8414 | 8.8411 |
| 1 | 12.58 | 7007 | 8.854664928 | 8.868 | 8.885 | 8.863 | 8.863 | 8.868 | 8.667 |
| 2 | 18.58 | 7233 | 8.886409167 | 8.879 | 8.891 | 8.875 | 8.874 | 8.880 | 8.879 |
| 3 | 24.58 | 7384 | 8.907070776 | 8.890 | 8.897 | 8.888 | 8.886 | 8.892 | 8.891 |
| 4 | 35.73 | 7299 | 8.895492631 | 8.905 | 8.905 | 8.904 | 8.901 | 8.909 | 8.907 |
| 5 | 38.74 | 7433 | 8.913684825 | 8.916 | 8.910 | 8.916 | 8.912 | 8.922 | 8.920 |
| Slope: |  |  |  | 1.85E−03 | 9.63E−04 | 2.02E−03 | 1.89E−03 | 2.08E−03 | 2.03E−03 |
| Blood Volume: |  |  |  | 6936 | 7137 | 6890 | 6898 | 6915 | 6913 |
| Mean |  |  |  | 8.891 | 8.901 | 8.893 | 8.888 | 8.890 | 8.886 |
| R^2 |  |  |  | 71.0% | 49.8% | 74.6% | 86.4% | 76.9% | 60.1% |
| Worst Point: |  |  |  | 3 | 3 | 3 | 2 | 3 | 3 |
| Residual Standard Error |  |  |  | 1.44% | 0.86% | 1.33% | 0.91% | 1.27% | 1.42% |

As further shown in FIG. 1, the blood volume/total body albumin analyzer 10 according to an exemplary embodiment of the present invention may include a quality control module 60, including an automated calibration system 62, an injectate verification system 64 and a remote diagnostics system 66.

The automated calibration system 62 insures that the gamma counter 12 is functioning at its optimal level. In particular, the energy window for the I-131 decay must be set correctly. Scintillation counters work by translating the energy of decay into counts in various "channels" that correspond to different energy levels. To efficiently count a particular kind of radiation (from a certain isotope, in this case I-131) the window must correspond to the spectrum of the decay. The ideal window will maximize the signal-to-noise ratio by including the peak(s) of the spectrum, and excluding the rest of the spectrum.

The automated calibration system 62 may use one Cesium (Cs-137) and one Europium (Eu-152) isotope to perform a calibration check and adjustment when needed. A multichannel analyzer (MCA) component of the gamma counter 12 separates energy into a set of evenly spaced channels. The channels of the MCA can be associated with specific energy levels by measuring radioactive sources with known energy peaks in their spectra. Calibration is a two-step process. The automated calibration system 62 may first use an integrated peak search algorithm to first find the 662 keV Cs-137 peak, and then query the multi-channel analyzer of the gamma counter 12 to determine at which channel the 662 keV Cs-137 peak was found. If the value of the channel is not [662]±/− a specified channel tolerance, the automated calibration system 62 may proceed to adjust the fine gain of the multi-channel analyzer such that channel [662] corresponds to the 662 keV Cs-137 peak. The automated calibration system 62 may then use the Eu-152 source to make a linear adjustment to the energy-to-channel curve such that channel [334] corresponds to the 334 keV Eu-152 peak. Note that [662] refers to the channel number associated with 662 keV. The MCA can have any number of physical channels, typically a power of 2 such as 512, 1024, 2048, etc.

The quality control module 60 may perform a series of measurements to ensure that the blood volume/total body albumin analyzer 10 is operating within approved parameters. For example, the quality control module 60 may measure one or more of the following: ambient background measurement check (this is a measurement with nothing in the detector—radiation should be relatively low), sample carriers contamination check (this is a measurement with just a sample carrier, but no sample in the carrier—radiation should be relatively low), standards check (I-131-tagged serum albumin standards used in individual BV tests) (this a measurement of the I-131 standards which are the basis for the BVA and TBA measurements, and which have known activity levels—detected counts should match expected levels), resolution and efficiency check (when counting I-131 standards, entire peak spectrum should fall into the window of channels, but the window should not be broader than the peak) and linearity test (when counting samples with differing known amounts of radioactivity(amt.x and amt.y), observed counts (counts.x and counts.y) must satisfy linearity within a desired tolerance—deviation from linearity can be expressed as abs ((counts.x/counts.y)*(amt.y/amt.x)−1)). For each of these measurements, results must be within defined ranges. User documentation may be provided to deal with out-of-range values (for example, by decontaminating the instrument, or moving it to another lower-background location).

The quality control module 60 may be configured to automatically run at a pre-determined time and frequency so as to eliminate the need for user involvement. The quality control module 60 may also keep an internal record of time that has elapsed since the last successful quality check and may maintain user accessible records. In an exemplary embodiment, the quality control module 60 can be configured to automatically initiate a quality control check if the time since the last successful quality control check exceeds a specified maximum time, such as, for example, 24 hours. The quality control module 60 may allow for an override and/or an abort of a scheduled quality control check.

The injectate verification system 64 may ensure that the I-131-tagged serum albumin injectate and standards for a given patient study are from the same lot number and same manufacturer before allowing the user to proceed with the study. Injectate verification may be accomplished by affixing a unique encrypted machine readable 2-D barcode to both the injectate and standards at the time of their manufacture. Prior to starting a test, the injectate verification system 64 may read each barcode and decrypt the information contained within to perform the verification step. The barcode read by the injectate verification system 64 may contain the following types of information: the year, day and month of manufacture, batch ID, serialization ID, manufacturer identification code, type (injectate or standard), and injectate brand, to name a few. The injectate verification system 64 may use the above information to automatically record the lot number of the injectate used for a given patient study. By doing so, the likelihood of an operator transcription error in regards to capturing lot number information may be eliminated.

In an exemplary embodiment of the invention, the injectate verification system 64 may keep an internal record of all lots for which standards have been quality control verified. If a barcode is read from a standard which has not been quality control verified, the injectate verification system 64 may instruct the user to perform a quality control test on the standard before proceeding to use it in a blood volume patient study. This check helps ensure the integrity and consistency of the test results.

The remote diagnostics system 66 may provide for remote monitoring via secure means the condition of the blood volume/total body albumin analyzer 10 and user usage patterns. Remote diagnostics may help diagnose a given symptom, issue or problem. Goals of remote diagnostics include improvement in the reliability of the installation, reduction of maintenance costs by avoiding unplanned maintenance and assisting in the identification of un-addressed user needs. Remote diagnostics includes the ability to conduct trend analysis and, via detection of any performance degradation, predict the failure moment via extrapolation. Remote diagnostics can be conducted by any secure, encrypted means, such as, for example, a secure, encrypted Internet connection, such as a Virtual Private Network (VPN) connection. Another exemplary embodiment may include a software facility for storing an encrypted version of the analyzer's operating data on a recording medium such as an optical disk, which may be physically transported to another location for review.

In an exemplary embodiment, the remote diagnostics system 66 may conduct trend analysis, in which a Chi-Square goodness of fit test is used to quantitatively judge whether the variances of a population of computed scintillation counter efficiency results match predictions to a specified confidence level.

In an exemplary embodiment, the remote diagnostics system 66 may perform spectrum capture, in which the energy spectrum of all samples that are counted in the course of conducting blood volumes & quality control tests are recorded. For diagnostic purposes, the recorded spectrum for any sample may be accessed and viewed remotely.

In an exemplary embodiment, the remote diagnostics system 66 may maintain a set of system logs that capture system events. The logs may be remotely viewed and queried for diagnostic purposes. Events may be classified as error, warning, information or security events. A system error event may be considered to be a significant problem, such as a failure to communicate with the multi-channel analyzer or an unexpected power loss. A system warning may be an event that is not significant, but might indicate a possible future problem. An information event may describe the successful execution of a system operation such as the loading of a software module, driver, or service. Security events may describe actions that indicate an attempt to tamper with the blood volume/total body albumin analyzer 10 or information stored within the device.

In an exemplary embodiment, the remote diagnostics system 66 may maintain a set of usage logs that capture generic user actions such as the pressing of a button, or clicking on an input field for the purpose of entering information. These logs may be remotely accessed and may be used to re-create user usage scenarios that occurred leading up to an issue or problem.

The blood volume/total body albumin analyzer 10 according to an exemplary embodiment of the invention may be configured to determine the ideal blood volume of an amputee patient. In this regard, correction factors may be used to reduce the predicted ideal blood volume and red cell volume. The corrections may be based on the assumption that the blood volume of a muscular tissue such as the leg or the arm has a higher blood volume/cc ratio (or ml ratio) than would be obtained if one were to take a theoretical slice through the trunk or abdomen. These are reasonable approximations considering the portion of the body weight which would be involved by the loss of a leg or an arm. The degree of uncertainty that would be created by the use of such a correction estimate would be approximately ±2%. The calculation may performed as follows:

1) Obtain the predicted normal blood volume based on the patient's height and weight as determined by the blood volume/total body albumin analyzer 10;

2) Apply the following correction factors:
 (a) below the knee amputation—3% for both white blood count and red cell volume;
 (b) above the knee—4% for white blood volume and red cell volume;
 (c) arm amputation—2% for white blood volume and red cell volume.

In an exemplary embodiment, blood volume/total body albumin analyzer 10 may have the ability to allow a user to perform a radio hematocrit. Normally, the hematocrit is measured by centrifuging a sample of whole blood in a narrow tube, and measuring the volume of the whole blood which is compressed into the lower end. This measurement has an accuracy limited by physical factors (particularly the ability to read/measure small distances on the tube) and has a precision of no more than +/−0.5%. A radio hematocrit can be performed using the blood volume/total body albumin analyzer 10 by measuring one or more samples of whole blood versus samples of spun plasma from the same samples, and taking the ratio of observed counts. This method provides at least two advantages in that it avoids the need for a separate hematocrit measurement and it allows for a greater accuracy in the hematocrit measurement, which is limited only by pipetting accuracy (in the range of +/−0.02%) and the length of counts that are observed.

Now that the preferred embodiments of the present invention have been shown and described in detail, various modifications and improvements thereon will become readily apparent to those skilled in the art. Accordingly, the spirit and scope of the present invention is to be construed broadly and not limited by the foregoing specification.

What is claimed is:

1. An automated total body albumin analyzer comprising a processor and a non-transitory computer-readable medium including instructions that are read by the processor to perform the following method:
 injecting radio-labeled albumin into the bloodstream of a human subject;
 collecting blood samples from the human subject over a time period after injection;
 gathering data related to a number of counts of radio-labeled albumin within each sample;
 receiving input of a baseline of expected ratio of amount of albumin in an intravascular system of the human subject to amount of albumin in an extravascular system of the human subject, wherein the baseline is a baseline curve based on a locally weighted scatterplot smoothing analysis of ratios of count values of radio-labeled albumin over a period of time after the radio-labeled albumin is initially injected into a control group of human subjects to count values of radio-labeled albumin at a time when the radio-labeled albumin is initially injected into the control group of human subjects;
 receiving input of albumin concentration of the human subject;
 calculating plasma volume of the human subject based on detected counts of radio-labeled albumin injected into the human subject;
 calculating an amount of intravascular albumin within the human subject based on the calculated plasma volume and the albumin concentration of the human subject;
 calculating an observed ratio of amount of albumin in the intravascular system of the human subject to amount of albumin in the extravascular system of the human subject at at least one time after injecting the radio-labeled albumin into the human subject; and
 calculating the total body albumin of the human subject based on the calculated intravascular albumin, the calculated observed ratio of amount of albumin in the intravascular system to amount of albumin in the extravascular system at the at least one time, and the baseline of expected ratio of amount of albumin in the intravascular system of the human subject to amount of albumin in the extravascular system of the human subject at the at least one time, wherein the calculated observed ratio is known to exhibit a consistent deviation from the baseline, and wherein the step of calculating the total body albumin is performed before rate of loss of albumin in the intravascular system of the human subject to the extravascular system of the human subject is stabilized.

2. The automated total body albumin analyzer of claim 1, wherein the at least one time comprises multiple times, and the method further comprises calculating an average value of the total body albumin calculated at the multiple times.

3. The automated total body albumin analyzer of claim 1, wherein the step of calculating plasma volume is performed using an automated blood volume analyzer.

* * * * *